United States Patent [19]

Kollmeyer

[11] 3,996,372
[45] Dec. 7, 1976

[54] INSECTICIDAL 1-ACYL-3-SUBSTITUTED-2-(NITRO(PHENYLTHIO)-METHYLENE)IMIDAZOLIDINES

[75] Inventor: Willy D. Kollmeyer, Modesto, Calif.
[73] Assignee: Shell Oil Company, Houston, Tex.
[22] Filed: Dec. 3, 1975
[21] Appl. No.: 637,251
[52] U.S. Cl. ............................ 424/273; 260/309.7
[51] Int. Cl.$^2$ ..................................... C07D 233/20
[58] Field of Search ................ 260/309.7; 424/273
[56] References Cited
UNITED STATES PATENTS 3,354,171   11/1967   Wehrmeister ................. 260/309.6
3,948,934   4/1976    Tieman et al. ................ 260/309.7

OTHER PUBLICATIONS

Isaksson et al. Chem. Abst. 1967, vol. 67, No. 81704r.
Kirkwood et al. Chem. Abst. 1954, vol. 48, columns 6968–6969.
Gompper et al. Chem. Ber. 1967, vol. 100, pp. 591–604.

Primary Examiner—Natalie Trousof

[57] ABSTRACT

Insecticidal 1-acyl-3-substituted-2-(nitro(phenylthio)-methylene)imidazolidines.

3 Claims, No Drawings

INSECTICIDAL 1-ACYL-3-SUBSTITUTED-2-(NITRO(PHENYLTHIO)-METHYLENE)IMIDAZOLIDINES

DESCRIPTION OF THE INVENTION

It has been found that useful insecticidal activity is possessed by certain amides of the formula:

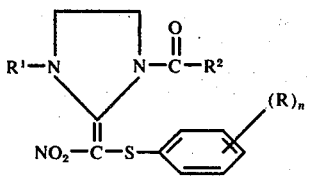

wherein $n$ is zero, 1 or 2, R is halogen, nitro, or alkyl or alkoxy of from one to six carbon atoms, $R^1$ is alkyl, alkenyl, haloalkenyl, alkynyl or cyanoalkyl each of up to ten carbon atoms, and $R^2$ is alkyl of from one to ten carbon atoms or is phenyl, or phenalkyl in which the alkyl moiety contains from one to four carbon atoms, or either of these substitued on the ring by from one to two of one or more of halogen, nitro, or alkyl or alkoxy of from one to six carbon atoms. Any aliphatic moiety present can be of straight-chain or branched-chain configuration.

Of particular interest, because of their insecticidal characteristics, are those compounds of sub-genus wherein $R^1$ is methyl, especially the class thereof wherein $R^2$ is alkyl and $n$ is zero.

For illustration, preparation of two particular species of the amides of the genus is described in the examples included hereinafter. Other typical particular species of this genus of amides include those wherein the symbols (referring to formula I) represent the following moieties, this manner of designating these species being accurate, yet pointing out the differences between the different species more clearly than if the entire, complicated name of each species were to be given:

| n | R | $R^1$ | $R^2$ |
|---|---|---|---|
| 1 | (4-) methoxy | 2-propenyl | methyl |
| 1 | (4-) methyl | 3-chloro-2-propenyl | benzyl |
| 0 | — | 2-propynyl | phenyl |
| 1 | (4-) chloro | cyanomethyl | methyl |
| 1 | (4-) chloro | methyl | methyl |
| 2 | (2,4-) dinitro | methyl | methyl |
| 1 | (4-) methoxy | methyl | methyl |
| 1 | (4-) methyl | methyl | methyl |
| 1 | (4-) chloro | methyl | methyl |
| 1 | (3-) chloro | methyl | methyl |
| 1 | (3-) nitro | methyl | methyl |
| 1 | (4-) nitro | methyl | methyl |

Compounds of the invention can be prepared by treating the precursor

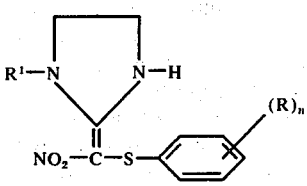

with the appropriate acid anhydride or with the appropriate acid chloride in the presence of a hydrogen halide acceptor, such as triethylamine, or other tertiary amine. Preparation of suitable precursors is described in application Ser. No. 510,100, filed Sept. 27, 1974, now U.S. Pat. No. 3,948,934. For the purpose of describing the preparation of these precursors, the pertinent portions of said application are incorporated herein.

Briefly, however, the needed precursors can be prepared by treating the precursor having hydrogen on the carbon atom of the nitromethylene moiety with the appropriate phenylsulfenyl chloride or bromide in the presence of a hydrogen halide acceptor. A solvent such as methylene chloride preferably is used, and the hydrogen halide acceptor suitably is a tertiary alkylamine, such as triethylamine, or an aromatic amine such as pyridine can be used both as solvent and hydrogen halide acceptor. The reaction is conveniently conducted by mixing the reactants at room temperature or somewhat below, and cooling if needed to maintain the temperature of the reaction mixture at or moderately above room temperature. Some of the phenylsulfenyl halides are known compounds. Others are readily prepared by direct halogenation of the appropriate thiol or disulfide, according to the procedure described by E. Kühle, Synthesis 1970, 561–580.

The precursor wherein hydrogen is present on the nitromethylene moiety can be prepared by several procedures:

Method A — treating a nitroketene dimethyl mercaptole (NKDM) with ethylenediamines, including suitably substituted ethylenediamines; R. Gompper and H. Schaefer, Berichte, 100, 591 (1967);

Method B — substituting a moiety on the NH function of 2-(nitromethylene)imazolidine (NMI); a method for preparing the latter kind of compound is diclosed in Gompper and Schaefer, supra.

In Method A, the reaction is carried out by mixing the reactants in a suitable solvent at a moderately elevated temperature under anhydrous conditions. Suitably, the reaction can be carried out at from about 50° to about 100° C. Often it may be convenient to conduct the reaction at the reflux temperature. Suitable solvents are the lower alkanols, particularly ethanol or isopropyl alchohol. In some cases it will be found desirable to employ a slight (5–10%) to moderate (50–75%) excess of the diamine reactant. The unsubstituted and appropriately substituted diamines are generally known materials.

In Method B, the N-substitution is conveniently effected by introducing the 2-(nitromethylene)imazolidine (NMI), which may be prepared by Method A, into a cold anhydrous mixture of a dispersion of sodium hydride in oil and dimethylformamide as solvent in an inert atmosphere and then treating the resulting mixture (containing the N-sodium derivative of NMI) with a halide of the moiety to be substituted; the reaction is general for alkylating agents. Suitably, addition of the halide is conducted at a temperature below about 10° C and is conveniently conducted at ice-bath temperature. It will be found desirable in many cases to employ a slight (5–25%) excess of the sodium hydride, and a slight (5–10%) to moderate (50–75%) excess of the halide.

The desired product in each case can be isolated from the crude reaction mixture and purified by conventional methods, such as filtration, extraction, crystallization and elution (chromatography).

Treatment of the precursor, II, with an acid anhydride to prepare a compound of the invention can be affected by heating the two materials together at a moderately elevated temperature — for example, from about 40° to about 150° C, using an inert solvent, if necessary. In some cases, an excess of the anhydride can be used as the solvent. Otherwise, a halogenated alkane, such as methylene chloride or 1,2-dichloroethane, is suitable.

Treatment of the precursor, II, with an acid chloride to prepare a compound of the invention can be effected by the same general techniques as described hereinbefore for treatment of the precursor having hydrogen on the carbon atom of the nitromethylene moiety with the phenysulfenyl halide.

Here, too, the desired product can be isolated from the crude reaction mixture and purified by conventional techniques, such as filtration, extraction, crystallization and elution (chromatography).

The preparation of compounds of this invention by these techniques is illustrated by the following examples of the preparation of particular species thereof. In all cases, the identity of the product and of the precursor employed was confirmed by appropriate analyses.

EXAMPLE 1

1-(3-methyl-2-(nitro(phenylthio)methylene)-1-imidazolidinyl)ethanone (1; $n = 0$, $R^1$ = methyl; $R^2$ = methyl)

A mixture of 16.52 grams of NKDM, 8.14 grams of N-methylethylenediamine and 200 milliliters of absolute ethanol was refluxed for 1.5 hours. The mixture was then cooled, and the reddish brown crystalline product that formed was removed by filtration. The product melting point: 142.5°–143.5° C. A 6.3 gram portion of the product was recrystallized from ethanol (charcoal) to give 4.8 grams of 1-methyl-2-(nitromethylene)imidazolidine (1A), as white needles, melting point: 142.5°–143.5° C.

14.6 g of phenylsulfenyl chloride was added dropwise to a cooled, stirred solution of 14.3 g of Compound 1A in 250 ml of pyridine. The mixture was allowed to stand overnight at room temperature, then excess pyridine was recovered on a rotary evaporator. The residue was treated with 250 ml of water and the mixture was extracted with methylene chloride. The combined extracts were dried and the solvent was evaporated to give a crystalline solid which was triturated with ethyl acetate, then ethanol to yield 1-methyl-2-(nitro(-phenylthio)methylene)imidazoline (1B) as a yellow solid, melting point: 170°–173°.

20 ml of acetic anhydride and 1.26 g of 1B were heated together at 100° for 1 hour. The resulting mixture was cooled on an ice-bath and filtered to give 1, as a yellow crystals, m.p.: 191°–193° (with decomposition).

EXAMPLE 2

1-benzoyl-3-methyl-2-(nitro(phenylthio)methylene)-imidazolidine (2; $n = 0$; $R^1$ = methyl; $R^2$ = phenyl)

0.71 g of benzoyl chloride was added to 1.26 g of 1B and 0.63 g of triethylamine in 25 ml of methylene chloride at 0°–20°. After stirring overnight at room temperature, the solvent was stripped. The solid residue was triturated with ice-cold methanol and then filtered to give 2, as a yellow solid, m.p.: 175°–178°.

Compounds of this invention are of particular interest for control of the larvae "caterpillar" or "worm" forms of insects of the genus Heliothis, such as *H. zea* (corn earworm, cotton bollworm tomato fruitworm), *H. virescens* (tobacco budworm). In tests that have been conducted representative compounds have exhibited substantial activity with respect to larvae of the corn earworm but low, or no, toxicity to other insects, such as the housefly, pea aphid, 2-spotted spider mite and mosquito larva.

Activity of compounds of this invention with respect to insects was determined by extablishing the $LC_{50}$ dosage (in milligrams of test compound per 100 milliliters of solvent required in the solution or suspension of test compound used as a spray) to kill 50% of the test insects. The liquid carrier was composed of 2 parts weight of acetone, 8 parts by volume of water and 0.05 parts by weight of Atlox 1045A, a wetting agent. The test insects were the housefly, corn earworm, mosquito, pea aphid and 2-spotted spider mite. Both of Compounds 1 and 2 were inactive or slightly active to the houseflies, aphids, mites and mosquito larvae. Both compounds were active with respect to the corn earworm.

The invention includes within its scope insecticidal compositions comprising an adjuvant — that is, a carrier, optionally a surface-active agent — and, as active ingredient, at least one insecticide of this invention. Likewise the invention includes also a method of combatting insect pests at a locus which comprises applying to the locus an effective amount of at least one insecticide of the invention.

The term "carrier" as used herein means a material, which may be inorganic or organic and of sythetic or natural origin, with which the active compound is mixed or formulated to facilitate its application to the plant, seed, soil and other object to be treated, or its storage, transport or handling. The carrier may be a solid or a liquid.

Suitable solid carriers may be natural and sythetic clays and silicates, for example natural silicas such as diatomaceous earths; magnesium silicates, for example, talcs; magnesium aluminum silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates; elements such as for example, carbon and sulfur; natural and synthetic resins such as, for example, coumarone resins, polyvinyl chloride and styrene polymers and copolymers; solid polychlorophenols; bitumen, waxes such as beeswax, paraffin wax, and chlorinated mineral waxes; degradable organic solids, such as ground corn cobs and walnut shells; and solid fertilizers, for example, superphosphates.

Suitable liquid carriers include solvents for the compounds of this invention and liquids in which the toxicant is insoluble or only slightly soluble.

Examples of such solvents and liquid carriers generally are alcohols, for example, isopropyl alcohol, ketones, such as acetone, methyl ethyl ketone, methyl isobutyl ketone and cyclohexanone; ethers; aromatic hydrocarbons such as benzene toluene and xylene; petroleum fractions such as kerosene, light mineral oils, chlorinated hydrocarbons, such as carbon tetrachloride, perchlorethylene, trichloroethane, including liquefied normally vaporous gaseous compounds. Mixtures of different liquids are often suitable.

If used, the surface-active agent may be an emulsifying agent or a dispersing agent or a wetting agent. It may be nonionic or ionic. Surface-active agents usually applied in formulating pesticides may be used. Examples of such surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; fatty acid salts of low molecular weight mono-, di- and trialkylamines; condensates of these with ethylene oxide and/or propylene oxide; condensation products of fatty alcohols or alkyl phenols for example, p-octylphenol or p-octylcresol, with ethylene oxide and/or propylene oxide; sulfates or sulfonates of these condensation products; alkali or alkaline earth metal salts, preferably sodium salts, of sulfuric or sulfonic acids esters containing at least 10 carbon atoms in the molecule, for example, sodium lauryl sulfate, sodium secondary alkyl sulfates, sodium salts of sulfonated castor oil, and sodium alkylaryl sulfonates such as sodium dodecylbenzene sulfonate; and polymers of ethylene oxide and copolymers of ethylene oxide and propylene oxide.

The compositions of the invention may be formulated as wettable powders, dusts, granules, solutions, emulsifiable concentrates, emulsions, suspension concentrates or aerosols. Encapsulated formulations and controlled release formulations also are contemplated, as are bait formulations. Wettable powders are usually compounded to contain 25, 50 or 75%w of toxicant and usually contain, in addition to solid carrier, 3–10%w of a dispersing agent and, where necessary, up to 10%w of stabilizer(s) and/or other additives such as penetrants or stickers. Dusts are usually formulated as a dust concentrate having a similar composition to that of a wettable powder but without a dispersant, and are diluted in the field with further solid carrier to give a composition usually containing ½–10%w of toxicant. Granules may be manufactured by agglomeration or impregnation techniques. Generally, granules will contain ½–25%w toxicant and 0–10%w of additives such as stabilizers, slow release modifiers and binding agents. Emulsifiable concentrates usually contain, in addition to the solvent, and when necessary, co-solvent, 10–50%w/v toxicant, 2–20%w/v emulsifiers and 0–20%w/v of appropriate additives such as stabilizers, penetrants and corrrosion inhibitors. Suspension concentrates are compounded so as to obtain a stable, non-sedimenting, flowable product and usually contain 10–75%w toxicant, 0–5%w of dispersing agents, 0.1–10%w of suspending agents such as protective colloids and thixotropic agents, 0–10%w of appropriate additives such as defoamers, corrosion inhibitors, stabilizers, penetrants and stickers, and as carrier, water or an organic liquid in which the toxicant is substantially insoluble; certain organic additives or inorganic salts may be dissolved in the carrier to assist in preventing sedimentation or as antifreeze agents for water.

Aqueous dispersions and emulsions, for example, compositions obtained by diluting a wettable powder or an emulsifiable concentrate according to the invention with water, also lie within the scope of the present invention.

The compositions of the invention may also contain other ingredients, for example, other compounds possessing pesticidal, herbicidal or fungicidal properties, or attractants, such as pheromones, attractive food ingredients, and the like, for use in baits and trap formulations.

These compositions are applied in sufficient amount to supply the effective dosage of toxicant at the locus to be protected. This dosage is dependent upon many factors, including the carrier employed, the method and conditions of application, whether the formulation is present at the locus in the form of an aerosol, or as a film, or as discrete particles, the thickness of film or size of particles, the insect species to be controlled and the like, proper consideration and resolution of these factors to provide the necessary dosage of active material at the locus being within the skill of those versed in the art. In general, however, the effective dosage of toxicants of this invention at the locus to be protected — i.e. the dosage to which the insect contacts — is of the order of 0.001% to 0.5% based on the total weight of the formulation, though under some circumstances the effective concentration will be as little as 0.0001% or as much as 2%, on the same basis.

I claim:

1. A compound of the formula:

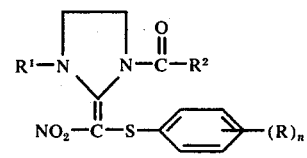

wherein $n$ is zero, 1 or 2, R is halogen, nitro or alkyl, or alkoxy each of from one to six carbon atoms, $R^1$ is alkyl, alkenyl, haloalkenyl, alkynyl or cyanoalkyl each of up to ten carbon atoms and $R^2$ is alkyl of from one to ten carbon atoms or is phenyl, or phenalkyl in which the alkyl moiety contains from one to four carbon atoms, or either of these substituted on the ring by from one to two of one or more of halogen, nitro or alkyl or alkoxy each of from one to six carbon atoms.

2. An insecticidal composition comprising an effective amount of a compound according to claim 1, together with adjuvant therefor 3. A method for controlling insects which comprises subjecting them to the action of an effective amount of a compound defined in claim 1.

* * * * *